US012533051B2

(12) United States Patent
Haller et al.

(10) Patent No.: US 12,533,051 B2
(45) Date of Patent: Jan. 27, 2026

(54) SELF PITCH MATCHING AS BASIS FOR ACOUSTIC COORDINATED RESET NEUROMODULATION

(71) Applicant: Aureliym GmbH, Bad Neuenahr-Ahrweiler (DE)

(72) Inventors: Markus Haller, Bad Neuenahr-Ahrweiler (DE); Christian Hauptmann, Bad Neuenahr-Ahrweiler (DE); Alexander Wegener, Bad Neuenahr-Ahrweiler (DE)

(73) Assignee: Aureliym GmbH, Bad Neuenahr-Ahrweiler (DE)

( * ) Notice: Subject to any disclaimer, the term of this patent is extended or adjusted under 35 U.S.C. 154(b) by 960 days.

(21) Appl. No.: 17/768,800

(22) PCT Filed: Jul. 10, 2020

(86) PCT No.: PCT/EP2020/069636

§ 371 (c)(1),
(2) Date: Apr. 13, 2022

(87) PCT Pub. No.: WO2021/073787

PCT Pub. Date: Apr. 22, 2021

(65) Prior Publication Data

US 2024/0099609 A1 Mar. 28, 2024

(30) Foreign Application Priority Data

Oct. 15, 2019 (DE) ..................... 10 2019 007 111.5

(51) Int. Cl.
*A61B 5/12* (2006.01)
*A61B 5/00* (2006.01)

(52) U.S. Cl.
CPC .............. *A61B 5/128* (2013.01); *A61B 5/123* (2013.01); *A61B 5/748* (2013.01)

(58) Field of Classification Search
None
See application file for complete search history.

(56) References Cited

U.S. PATENT DOCUMENTS 5,795,287 A 8/1998 Ball et al.
9,532,736 B2 1/2017 Rush

FOREIGN PATENT DOCUMENTS

EP 3184046 A1 6/2017
EP 3203910 B1 11/2018
(Continued)

OTHER PUBLICATIONS

"International Search Report and Written Opinion mailed Sep. 1, 2020 in corresponding International Application No. PCT/EP2020/069636 with the International Filing Date of Jul. 10, 2020".
(Continued)

*Primary Examiner* — Jay B Shah
(74) *Attorney, Agent, or Firm* — ALG Intellectual Property, LLC

(57) ABSTRACT

An illustrative method includes determining a preliminary estimate of the patient's tinnitus tone by allowing the patient to listen to and vary frequency and intensity of a first test tone within a predetermined first frequency range and a predetermined first intensity range to approximate the first test tone to the patient's tinnitus tone; defining a second frequency range and a second intensity range around the preliminary estimate of the patient's tinnitus tone; and determining a final estimate of the patient's tinnitus tone by allowing the patient to listen to and vary frequency and intensity of a second test tone within the second frequency range and the second intensity range to approximate the second test tone to the patient's tinnitus tone.

16 Claims, 11 Drawing Sheets

(56) References Cited

FOREIGN PATENT DOCUMENTS

| | | | |
|---|---|---|---|
| KR | 101636949 | B1 | 7/2016 |
| WO | 2014109762 | A1 | 7/2014 |
| WO | 2018024374 | A1 | 2/2018 |
| WO | 2018028828 | A1 | 2/2018 |
| WO | 2018024374 | A8 | 3/2018 |

OTHER PUBLICATIONS

Chamoso, et al.,"A Device Supporting the Self Management of Tinnitus", Apr. 1, 2017, Annual International Conference on the Theory and Applications of Cryptographic Techniques, Eurocrypt 2018, Stringer, Berlin, Heidelberg, p. 399-410, XP047410695 [retrieved Apr. 1, 2017].

Hauptmann, et al.,"Validation of a Mobile Device for Acoustic Coordinated Reset Neruomodulation Tinnitus Therapy", Journal of the American Academy of Audiology, vol. 27, No. 09, Oct. 6, 2016, pp. 720-731, XP055724032.

Tass, et al.,"A model of desynchronizing deep brain stimulation with a demand controlled coordinated reset of neural subpopulations", Biol Cybern 89(2):81-88, (2003).

Tass, et al.,"Counteracting tinnitus by acoustic coordinated reset neuromodulation", Restorative Neurology and Neuroscience 30(2):137-159, (2012).

Tass, et al.,"Long-term anti-kindling effects of desynchronizing brain stimulation: a theoretical study", Biol. Cybern 94 (1):58-66 (2005).

Tass, et al.,"Unlearning tinnitus-related cerebral synchrony with acoustic coordinated reset stimulation: theoretical concept and modelling", Biol. Cybern. 106(1):27-36 (2012).

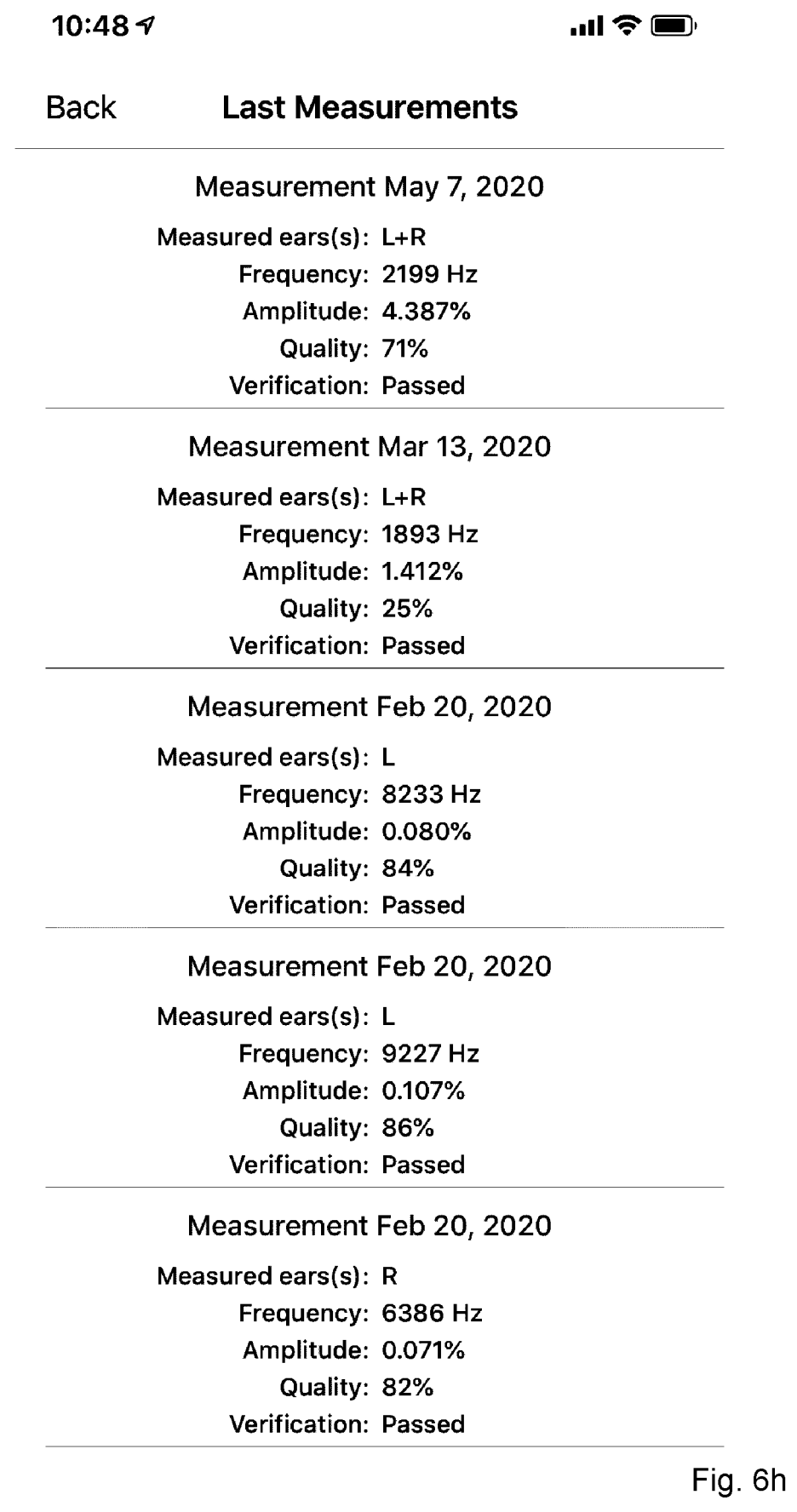

10:48

Back Last Measurements

Measurement May 7, 2020

Measured ears(s): L+R
Frequency: 2199 Hz
Amplitude: 4.387%
Quality: 71%
Verification: Passed Measurement Mar 13, 2020

Measured ears(s): L+R
Frequency: 1893 Hz
Amplitude: 1.412%
Quality: 25%
Verification: Passed Measurement Feb 20, 2020

Measured ears(s): L
Frequency: 8233 Hz
Amplitude: 0.080%
Quality: 84%
Verification: Passed Measurement Feb 20, 2020

Measured ears(s): L
Frequency: 9227 Hz
Amplitude: 0.107%
Quality: 86%
Verification: Passed Measurement Feb 20, 2020

Measured ears(s): R
Frequency: 6386 Hz
Amplitude: 0.071%
Quality: 82%
Verification: Passed

Fig. 6h

SELF PITCH MATCHING AS BASIS FOR ACOUSTIC COORDINATED RESET NEUROMODULATION

The present invention resides in the field of tinnitus diagnosis and treatment and specifically concerns means and methods for pitch matching.

Acoustic coordinated reset (CR) neuromodulation therapy is a form of noninvasive neuromodulation therapy for treating primary tinnitus, in particular, the frequency-specific, often tonal tinnitus commonly seen in these patients. See, for example, "Counteracting tinnitus by acoustic coordinated reset neuromodulation," Restor. Neurol. Neurosci. 30(2): 137-159. Tass et al., 2012.

Acoustic CR neuromodulation uses acoustic signals that stimulate the auditory neural tracts as they account for hearing level and psychoacoustic characteristics of the tinnitus percept (Tass et al., 2012, supra). These techniques employ well-accepted neuroplasticity principles and were developed using computational modeling. See, for example, "A model of desynchronizing deep brain stimulation with a demand controlled coordinated reset of neural subpopulations," Biol Cybern 89(2):81-88, Tass, 2003. See also "Long-term anti-kindling effects of desynchronizing brain stimulation: a theoretical study," Biol. Cybern 94(1):58-66, Tass, P. A., Majtanik M., and "Unlearning tinnitus-related cerebral synchrony with acoustic coordinated reset stimulation: theoretical concept and modelling," Biol. Cybern. 106(1):27-36, Tass and Popovych, 2012.

Using the systematic tonotopic organization of the peripheral and central auditory system in the auditory cortex in the temporal lobe, acoustic tones, typically four different frequencies centered around the characteristic frequency of the patient's tinnitus percept, are determined and delivered in non-simultaneous sequences several hours per day for several weeks (Tass et al., 2012, supra). The four tones are designed to activate different areas of the central auditory system in a coordinated manner.

To provide a successful therapy, a precise pitch matching, i.e. the measurement of the dominant tinnitus frequency, is necessary. In the first years of commercial usage of the acoustic coordinated reset therapy, a simple pitch matching process was used, where the patient was allowed to use dial wheels to adjust the intensity and frequency of an external test tone. By this, the patient had to find an external test tone, that matches his tinnitus best. Some patients were able to accomplished this task, but others were not. Therefore, several years ago a more guided process was developed, resulting in reliable and precise results (cf. patent family of granted European patent 3 203 910 B1). This guided process includes several steps, namely bracketing, similarity measure, pairwise comparison and fine-tuning. Such a pitch matching gives very reliable results, the method was validated and results were published. The disadvantage of this advanced pitch matching method is the time it requires. Typically, a pitch match takes 45-60 minutes for a trained patient, while untrained patients could take even longer.

Since lengthy pitch match procedures result in fatigue and therefore reduced precision, there is a need for methods that can be completed faster. Moreover, it would be desirable to have a pitch matching method that does not require the assistance of an expert so that it could be performed and, if necessary repeated, at any time, in particular at a time when a subject's attention is high. In addition, it would be advantageous to know how reliable the results obtained from such method are.

The problem is solved by the invention disclosed herein, in particular by the subject-matter as defined in the appended claims.

A first aspect of the present invention pertains to a method of determining the pitch of a patient's tinnitus tone. The method comprises the steps:

determining a preliminary estimate of the patient's tinnitus tone by allowing the patient to listen to and vary frequency and intensity of a first test tone within a predetermined first frequency range and a predetermined first intensity range to approximate the first test tone to the patient's tinnitus tone;

defining a second frequency range and a second intensity range around the preliminary estimate of the patient's tinnitus tone; and determining a final estimate of the patient's tinnitus tone by allowing the patient to listen to and vary frequency and intensity of a second test tone within the second frequency range and the second intensity range to approximate the second test tone to the patient's tinnitus tone.

The method of the invention is easy and does not require expert knowledge or the presence of an expert. It can thus be carried out by the patient at home at a time when the patient feels well and fresh. Moreover, the method is fast and thus does not lead to fatigue. The results obtained by the method are thus precise and reliable.

A patient as defined herein is a human, who has been diagnosed with or who is suspected of having subjective tinnitus. The patient preferably has a tinnitus that is characterized by a single, i.e. only one, dominant tinnitus tone. That is, the patient does not hear two or more tinnitus tones simultaneously of similar intensity and the patient's tinnitus tone does not change rapidly over time. A rapid change over time herein means a change within few hours, a few days or weeks, for instance within less than 6 weeks, preferably less than 4 weeks, more preferably less than 2 weeks, yet more preferably less than 1 week and most preferably less than 3 days.

The tinnitus tone as understood herein is characterized by the pitch (i.e. frequency) and the intensity of the patient's tinnitus. In a case where a patient hears multiple tinnitus frequencies simultaneously, any one, preferably the predominant one, of said plurality of frequencies defines the tinnitus tone. In a case where a patient's tinnitus tone changes over time, the method of the invention can only provide a snapshot of the current tinnitus tone. If the final estimate shall be used for neuromodulation-based therapy, it may thus be advisable to repeat the method at regular intervals as long as the therapy continues. In many cases, patients' tinnitus tones have a pitch ranging within 200 and 14.000 Hz, and an intensity ranging within 0 to 20 dB above hearing level (HL), although there might be cases, where the pitch and/or the intensity lie outside said ranges.

The term "intensity", when used herein in the context of the tinnitus tone, denotes a level how intense the patient perceives the tinnitus tone. The intensity of a patient's tinnitus tone corresponds to the intensity of an external test tone having the same frequency as the patient's tinnitus tone, which the patient perceives of the same intensity. The term "intensity", when used herein the context of a test tone, means the amplitude (volume) of the test tone at the patient's ear(s), irrespective how intense the patient perceives the tone.

In accordance with the method of the invention, a preliminary estimate of the patient's tinnitus tone is determined in a first step. For this purpose, a first test tone is played. The patient listens to the first test tone and varies its frequency and intensity (amplitude) within predetermined ranges.

If no information about the patient's tinnitus tone is available, the first test tone typically ranges from 200 Hz to 10000 Hz, but can also include higher frequencies (e.g. 200 Hz to 14000 Hz), although many patients might not be able to perceive such high frequencies, even at highest sound output of the device. In some cases, some information with regard to the patient's tinnitus tone might be available and the first frequency range could be limited (as disclosed herein). In any case, the first frequency range includes the pitch of the patient's tinnitus tone.

With respect to the first intensity range, it is perceived that the minimal and maximal intensity of the test tone may range from a fixed minimal to a fixed maximal value, for instance 0 to 60 dB HL, or 0% to 100%, relative to the maximal output that a respective device can deliver to the patient's ear(s). Preferably, the first intensity range is selected based on the threshold of perception (as further described below). In such case, the range is preferably selected so as to include the threshold of perception and extend from the threshold towards lower and higher intensities. For instance, the minimal boundary could be represented by the threshold minus 5 dB sound intensity and the maximal boundary could be represented by the threshold plus 20 dB sound intensity.

When the patient detects that the first test tone is closest to the patient's tinnitus tone, the patient confirms this tone (frequency and intensity) as the preliminary estimate of the patient's tinnitus tone. The preliminary estimate of the patient's tinnitus tone is then used in a second step to define the second frequency range and the second intensity range.

The second frequency range is preferably defined to extend around, i.e. above and below, the preliminary estimate. The advantage of this is that an approximation in either direction is possible in the third step. Non-limiting examples include two octaves below and two octaves above the preliminary estimate as respective lower and upper frequency limits, one octave below and one octave above the preliminary estimate as respective lower and upper frequency limits, and even more narrow ranges.

In order to allow an approximation of the intensity in the third step, also the second intensity range is preferably defined to extend around, i.e. above and below, the preliminary estimate. Moreover, the second intensity range may be identical to or different than the first intensity range. To increase sensitivity, it may be narrowed in comparison to the first intensity range. Non-limiting examples include minus and plus a predetermined value, e.g. 5 dB, from the preliminary estimate, or setting the second intensity range to be at least 10%, at least 20%, at least 30%, at least 40%, at least 50%, at least 60%, or at least 70% smaller than the first intensity range. In another example, the intensity range might by plus/minus 10 dB of the slightly varied intensity of the preliminary estimate.

In a preferred embodiment, the second frequency range and/or the second intensity range extend(s) non-symmetrically from the frequency and/or the intensity of the preliminary estimate. For examples, the frequency range may extend at least 20%, at least 30%, at least 40%, or at least 50%, more in the minus frequency direction than in the plus frequency direction, or vice versa. In another example, the frequency range might by 0.5 to 2.0 times the slightly varied frequency of the preliminary estimate. This means, in a case where the patient varies the frequency and intensity of the second test tone on a two-dimensional plane (e.g. on a screen), where the position in a first direction reflects the frequency and the position in a second direction reflects the intensity, the middle position does not reflect the frequency and/or the intensity of the preliminary estimate. Thereby, it is avoided that the patient simply selects the middle position and hence the preliminary estimate as the final estimate.

In the third step, the final estimate of the patient's tinnitus tone is determined. For this purpose, the second test tone is played. The patient listens to the second test tone and varies its frequency and intensity (amplitude) within the second frequency and intensity ranges. When the patient detects the second test tone to be closest to the patient's tinnitus tone, the patient confirms this tone (frequency and intensity) as the final estimate of the patient's tinnitus tone.

The final estimate of the patient's tinnitus tone can then be used as a basis for acoustic coordinated reset (CR) neuromodulation.

The method of the invention may be performed for each of the patient's ear separately, or for both ears simultaneously. In the latter case, it is preferred that the first and second test tones are delivered to both ears with the same perceived intensities.

The term "same perceived intensity" as used herein refers to intensities, which the patient perceives of substantially the same intensity. For example, a test tone of a given frequency needs to be delivered to the patient's right ear at a different intensity (amplitude) than to the patient's left ear due to different hearing ability between both ears. In another example, due to different hearing ability of the same ear, a test tone of a first frequency needs to be delivered to the patient's right ear at a different intensity (amplitude) than a test tone of a second frequency to achieve the same perceived intensity between the different frequencies.

The method of the invention is preferably implemented on a digital processing unit of an electronic device, in particular a handheld. The electronic device comprises an output unit for delivering the test tones to the patient; and a user interface for allowing the patient to vary the frequency and the intensity (amplitude) of the test tones.

In a preferred embodiment, the user interface comprises a touch screen defining a two-dimensional plane, which is configured so that sliding in a first dimension leads to an increase or decrease of the frequency and sliding in a second dimension leads to an increase or decrease of the intensity (amplitude). The second dimension is preferably orthogonal to the first dimension. In order to allow a sufficiently high precision of the measurement, the touch screen has preferably a minimum resolution of 1200×500 pixels.

In a further preferred embodiment, the first frequency range is different to the second frequency range and/or the first intensity range is different to the second intensity range. Thereby, it is avoided that the position of the final estimate does not correspond to the position of the preliminary estimate of the patient's tinnitus tone. The risk that the position incorrectly influences the result is decreased. Moreover, it is preferred that the second frequency range is smaller than the first frequency range and/or the second intensity range is smaller than the first intensity range. As an advantage, the sensitivity of the measurement can be increased.

According to a preferred embodiment of the present invention, the first frequency range and the first intensity range are determined based on the patient's masking level. The term "masking level" as used herein denotes the lowest intensity of a given frequency band required to mask the patient's tinnitus tone. The patient's masking level may be determined by a test using band-pass filtered white noise.

In a preferred embodiment, the masking level is determined by allowing the patient to listen to at least one frequency band individually and increase intensity of each of the at least one frequency band until the patient detects that one of the at least one frequency band masks the patient's tinnitus tone. Preferably, the patient is allowed to listen to a plurality, for instance, at least 3, preferably at least 4, most preferably at least 5 noise bands and/or at most 27, preferably at most 12, more preferably at most 10, most preferably at most 8 noise bands. For allowing the patient to perform the test at home, in little time, in an easy way and yet in a reasonable resolution, 4 to 6, in particular 5, noise bands are most preferred. In the test, the patient is exposed to each of the noise bands sequentially and allowed to increase the intensity (amplitude) until the patient detects the tinnitus tone to be masked. If the pitch of the patient's tinnitus is in a frequency range of the noise band, there is a high probability that the patient's tinnitus is masked, i.e. no longer perceptible, by this noise band. Detected volume and noise band is then used as a basis for determining the first frequency range and the first intensity range. For example, the frequencies of the noise band where masking was observed can be used as the first frequency range (optionally extended by some Hz in both directions), and the corresponding intensity extended by some dB in both directions (or plus/minus 30%) can be used as the first intensity range.

Since the patient may perceive different frequencies as of different intensities (as explained above), it is preferred that the intensities are adapted to the patient's individual hearing ability. Accordingly, it is preferred that intensities (amplitudes) within the first intensity range and/or intensities (amplitudes) within the second intensity range are scaled relative to same perceived intensities. In the present case, the same perceived intensities are intensities (amplitudes), which the patient perceives of substantially the same intensity at frequencies within the first frequency range and/or at frequencies within the second frequency range.

Tests for determining the same perceived intensities are known to a person skilled in the art. A preferred test in the context of the present invention involves a determination of the patient's threshold of perception for different frequencies. The different frequencies include and/or allow extrapolation to the frequencies within the first and/or second frequency range. For example, the patient's threshold of perception for a plurality of test tones covering a plurality of frequencies adjacent and/or within the first frequency range and/or covering a plurality of frequencies adjacent and/or within the second frequency range is determined in order to scale the intensities to the same perceived intensity.

The deviation of the preliminary estimate and the final estimate can be used to define a quality of the result. If both information is very similar, the information is of high quality, if the information differs strongly, the quality is low. Hence, according to a preferred embodiment of the present invention, the method further comprises determining a measure reflecting the quality (reliability) of the measurement. To this end, a deviation of the preliminary and the final estimate of the patient's tinnitus tone is calculated. Based on the deviation, reliability of the final estimate of the patient's tinnitus tone can be determined, wherein the reliability of the final estimate of the patient's tinnitus tone is defined to be higher the smaller the deviation, or vice versa. According to a preferred example, a sum of a factorized deviation in a frequency and intensity space is calculated and used as quality measure (as disclosed further below). It is further envisaged that the quality measure is based on both the deviation (e.g. factorized deviation) and an evaluation by the patient, such as the patient's answers to a questionnaire relating to the quality of the pitch matching result (as disclosed further below). The method may further comprise performing at least one pair-wise testing, wherein in each of the at least one pair-wise testing the patient is allowed to listen to one pair of tones, the one pair of tones consisting of the final estimate of the patient's tinnitus tone and a test tone different thereof, and to choose the tone which closer matches the patient's tinnitus tone. In this step, the patient listens to pairs of tones, one is the test tone and the other one is the final estimate. After listening to one pair of tones, the patient is asked to identify the tone that fits his tinnitus best, and so forth.

The test tones that are compared to the final estimate may include without limitation: one octave up and one octave down (to test for octave confusion), 1.4 times the second frequency, 0.766 times the second frequency, 1.1 times the second frequency, 0.9 times the second frequency, 0.95 times the second frequency or 1.05 times the second frequency.

Preferably, the test tone(s) intensity is/are adapted to have the same perceived intensity with the final estimate of the patient's tinnitus tone. That is, the corresponding intensities are chosen such that the test tone(s) and the final estimate are perceived as of similar intensity (as defined herein).

The at least one pair-wise testing may be used as a validation step. In accordance with this embodiment, the method is registered as passed only if the patient has chosen the final estimate of the patient's tinnitus tone as the tone which closer matches the patient's tinnitus tone in the majority, preferably in all, of the at least one pair-wise testing.

According to a second aspect, the problem is solved by a non-transitory storage medium storing instruction that are executable by a digital processing device to perform the method of the invention and the various embodiments thereof. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth.

According to a third aspect, the problem is solved by a computer program comprising program code means for causing a digital processing device to perform the method of the invention and the various embodiments thereof, when the computer program is run on a digital processing device.

According to a fourth aspect, the problem is solved by a digital processing device for performing the method of the invention and the various embodiments thereof. The digital processing device may be a handheld device (e.g., a personal data assistant or smartphone), a notebook computer, a desktop computer, a tablet computer or device, a remote network server, or so forth. Preferably, the digital processing device is a handheld device, in particular a smartphone. The digital processing device may comprise an output unit for delivering test tones to a patient, for example a loudspeaker and/or headphones connected to the digital processing device. The digital processing device may further comprise a user interface for allowing the patient to vary frequency and intensity of the test tones such as a touch screen or a screen with a input device (e.g. mouse). The digital processing device may further comprise a control unit in functional communication with the output unit and the user interface, the control unit comprising a digital processing unit for performing the method of the invention and the various embodiments thereof.

According to a preferred embodiment of the invention, the user interface comprises a touch screen defining a two-dimensional plane. Preferably, the touch screen is configured so that sliding in a first dimension leads to an increase or decrease of the frequency and sliding in a second dimension leads to an increase or decrease of the intensity.

The various features and embodiment defining the first aspect of the invention shall be understood to define according features and embodiments of the second, third and fourth aspects of the invention, and vice versa.

Further aspects, embodiments and advantages of the present invention become apparent from the following detailed description, the figures and claims, which follow after the brief description of the drawings.

FIG. 6*a-h* illustrates functionalities of the present invention according to various embodiments of the invention, implemented as a computer program (app) executed by a digital processing device (smartphone).

The present invention allows a health care professional or patient perform an accurate pitch matching within a short period of time, and provide input for neuromodulation-based therapies configured to treat subjective tinnitus. In the following, selected features and embodiments of the present invention as disclosed herein are described.

The method of the present invention (also referred to herein as pitch matching tool) is preferably implemented on a digital processing device (herein also referred to as electronic device or device), which has an appropriate user interface and high-quality sound output. As user interface, a touch screen with case sensitive user interfaces ideally support the pitch matching process. The present invention is not restricted to particular devices; most smartphones have both a high-resolution touch screen and a high-quality sound output, which renders them suitable for the present invention. The device may offer a comprehensive training and help function, to allow that an untrained patient can use the device without expert assistance.

As the patient may perceive different frequencies as of different intensity, information how intense a patient perceives different intensities may be collected in an initial step. To possible approaches are described in the following.

A first approach is based on band-pass filtered white noise. Although one may use 10, 12 or up to 27 noise bands, it is preferred that 5 noise bands are used. This allows for better handling to be done by the patient itself and at home. The 5 noise bands may be defined by the following low and high cut-offs:

Band 1: 100-3.700 Hz
Band 2: 3.700-5.300 Hz
Band 3: 5.300-7.700 Hz
Band 4: 7.700-12.000 Hz
Band 5: 12.000-15.500 Hz The stopband attenuation may be 60 dB. The term stopband defines the difference in power of the actual passband and the lower level outside the passband.

A (slight) overlap is possible. In particular, the used filters to realize the noise bands may not have an abrupt reduction of power to the stopband level at e.g. 3.700 Hz for the first band. Instead, the filter may have certain characteristics resulting in a certain slope of the spectrum resulting in an overlap.

Figure 1:
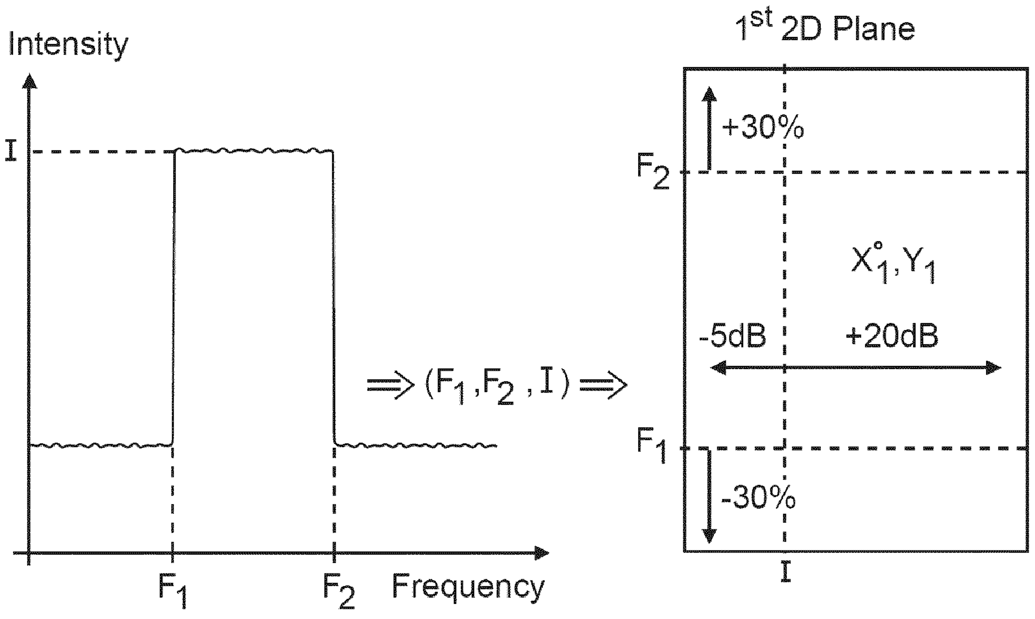
FIG. 1 illustrates a masking level-based approach for determining first intensity and frequency ranges according to one embodiment of the present invention.

The patient may then be exposed to each of these noise bands and asked to slowly increase the volume. If the tinnitus is in the frequency range of the noise band, there is a high probability that the patient's tinnitus is masked, i.e. no longer perceptible, by this noise band. The lower and upper frequency limits of the noise band where this masking was observed can then be used to determine the lower and upper frequency limits of the first frequency range. For instance, the lower and upper frequency limits $F_1$, $F_2$ of the noise band may by extended by 30% as shown in the example illustrated in FIG. 1. In this example, the minimal intensity I at which masking has been detected is extended by −5 dB and +20 dB to define the first intensity range. On the right, the first intensity and frequency ranges are plotted in a 2D plane, which, in preferred embodiments, illustrate a screen, preferably a touch screen, on which the patient can subsequently vary frequency and intensity of the first test tone by moving a button (e.g. a smaller circle) on the touch screen.

According to a second approach (herein also referred to as audiogram-like test), the patient identifies the threshold of perception for several test tones. The test tones might range from 200 Hz to 10.000 Hz; for example tones with frequencies 200 Hz, 400 Hz, 1.000 Hz, 2.000 Hz, 4.000 Hz, 6.000 Hz, 8.000 Hz, 10.000 Hz can be used. Even higher frequencies (up to 14.000 Hz) can be used, but many patients might not be able to perceive such tones, even at highest sound output of the device. The threshold of perception for the different frequencies thus determined can then be used to determine the first frequency and intensity ranges.

Figure 2:
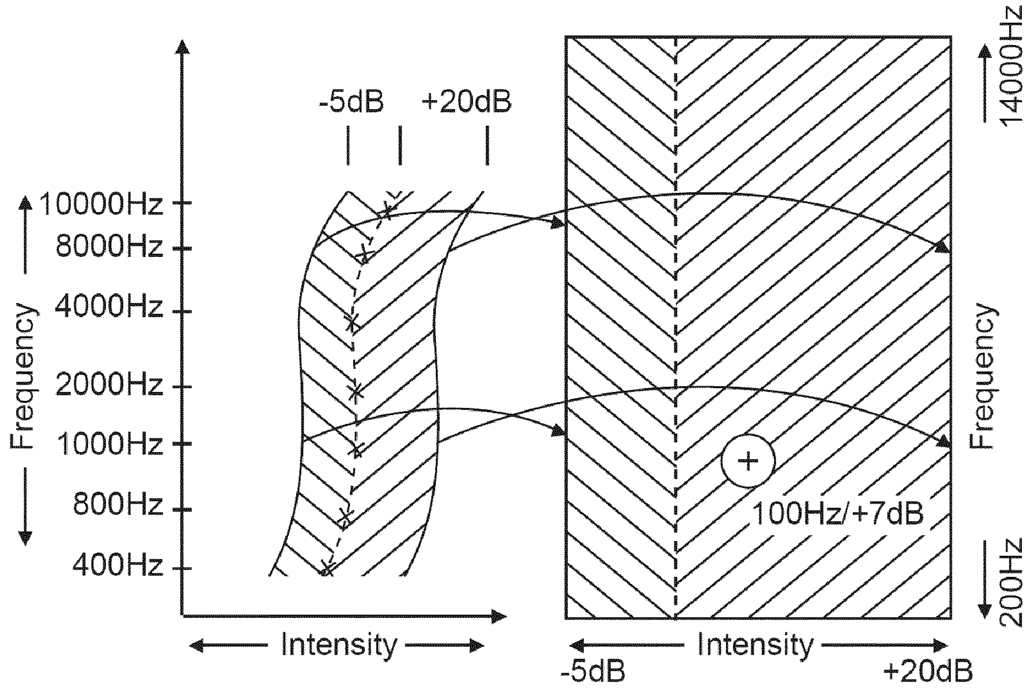
FIG. 2 illustrates an approach for determining first intensity and frequency ranges based on threshold of perception determined for different frequencies, according to one embodiment of the present invention.

For instance, as shown in the example illustrated in FIG. 2, the determined frequency-dependent threshold of perception (amplitude in %) is plotted over the respective frequency to define a curvature. This curvature shows that a frequency of ca. 4.000 Hz is perceived at a relatively low amplitude, whereas the patient hears lower and higher frequencies only at higher amplitudes. Moreover, the curvature is used to determine an upper and a lower corridor, which respective end points define the first intensity range. The lower corridor is defined by the curvature minus a certain dB value (5 dB in the example of FIG. 2), and the upper corridor is defined by the curvature plus a certain dB value (20 dB in the example of FIG. 2).

In some cases, it might be advantageous to allow the device to play the test tones, in particular, frequencies above 10 kHz, with maximum output volume, so that hearing-impaired patients may still hear the test tones.

The above measurement is preferably done for the left and the right ear separately. The output might be threshold information in dB SPL, dB HL or % sound output. For the functioning of the present invention, even the simplest realization (% sound output) would result in a good frequency match of the tinnitus.

Before starting with the first step, the patient may select, if the assessment is done for the left or right ear alone, or for both ears at the same time. Then, the patient moves a button on a two-dimensional plane (e.g. by moving the patient's finger on a touch screen). A first direction (e.g. x-direction) indicates the intensity of the tone, a second direction (e.g. y-direction) indicates the frequency of the first test tone. As output, either sinusoidal tones, or narrow bandwidth tones, or peaked noisy tones are used. The minimal and maximal intensity of the first test tones should be chosen to maximally support the patient in this process. A simple choice would be 0% intensity on the left boundary and 100% intensity on the right boundary (cf. FIG. 3).

A more complex, but better choice would be to use the audiogram-like test result to define the boundaries. E.g. the left (minimal value) boundary could be represented by threshold minus 5 dB sound intensity and the right (maximal value) boundary could be represented by the threshold plus 20 dB sound intensity. The boundaries may be defined for each frequency step independently, using the audiogram-like test information and interpolation. Referring again to FIG. 2, a determination of the first frequency and intensity range can be based on the threshold of perception determined for different frequencies. The x-axis of the graph on the left illustrates the intensity in terms of the amplitude (as shown in FIG. 2), whereas the x-axis of the 2D plane on the right illustrates the perceived intensity. This means, the frequencies lying on a vertical line are perceived by the patient of the same intensity.

For frequencies above 10.000 Hz it might be advantageous to use 100% as maximal output, therefore, the right boundary may smoothly increase from the 10.000 Hz maximal boundary (threshold plus 20 dB) to 100% output. If the test is performed for the left and right ear at the same time (stereo), the intensity boundaries are independently determined and the first intensity range is independently defined for the left ear and the right ear, resulting in the left and right ear to be balanced in intensity.

In an alternative approach, the psychoacoustic loudness scaling is envisaged. For example, if the hearing threshold of left and right differs more than a certain value to one frequency or few frequencies, e.g. by 15 dB, the pitch matching for both ears at the same time is not available and separate pitch matching has to be done for left and right.

Alternatively, the psychoacoustic loudness scaling is considered to adjust the upper intensity boundary in such a way, that the left and right tone is perceived as of same intensity even if there is a significant difference in the hearing threshold.

Figure 3:
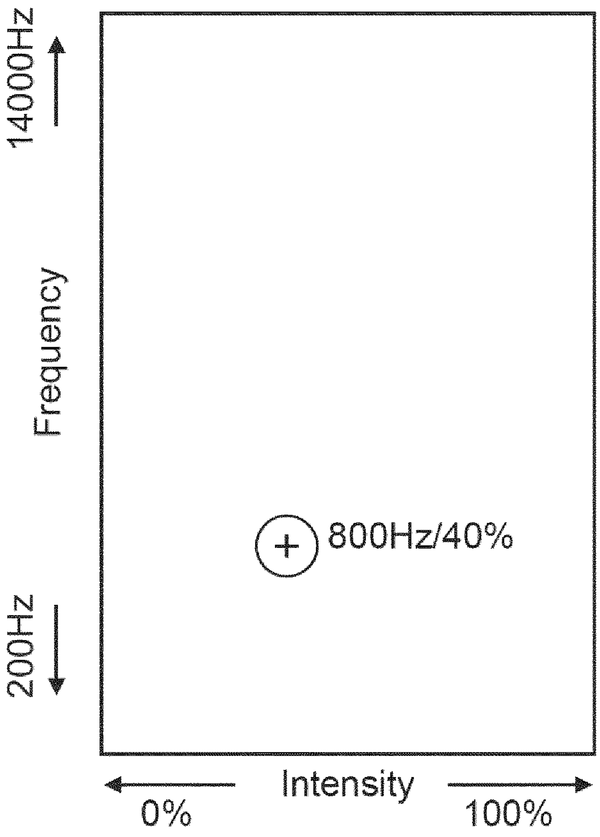
FIG. 3 illustrates a technical implementation allowing the patient to vary frequency and intensity simultaneously in a 2D plane, according to a preferred embodiment of the invention.

With respect to the first frequency range, the minimal and maximal frequency is chosen to cover the possible tinnitus frequencies, for example 200 Hz could be chosen as lower limit (bottom) and 14.000 Hz could be chosen as upper limit (top) (cf. FIG. 3).

The intensity scale may be a linear scale but is preferably a logarithmic scale, such that similar distances on the two-dimensional plane would be perceived as the same intensity changes. The frequency scale may be a linear scale but is preferably a logarithmic scale, such that similar distances on the two-dimensional plane would be perceived as the same frequency changes.

When the patient takes his finger from the button (e.g. by detaching the finger from the touch screen), the tone will stop. The tone will start again, when the patient touches the button. The start and stop of the tone may be smoothed by a short fade out and fade in. This function will allow the patient to concentrate on his tinnitus for few seconds, before the comparison with the test tone is continued.

The output of the first step is a first information about the tinnitus frequency and tinnitus intensity, herein referred to as the preliminary estimate of the patient's tinnitus tone.

Figure 4:
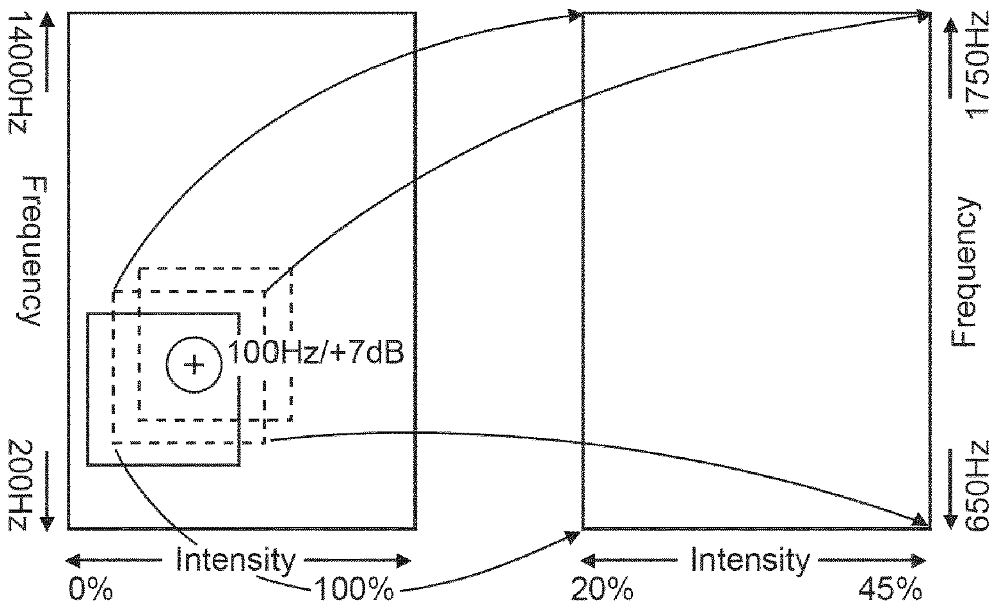
FIG. 4 illustrates an approach to define the second frequency and intensity ranges based on the preliminary estimate of the patient's tinnitus tone, according to one embodiment.

In a second step, the frequency limits are chosen to be around the frequency result of the first step (cf. FIG. 4).

For example, two octaves below and two octaves above the first frequency information can be chosen as lower and upper frequency limit, respectively. Alternatively, one octave below and one octave above the first frequency information can be chosen as lower and upper frequency limit, respectively. More narrow arrangements around the first frequency information might be possible as well. The intensity boundaries might be the same as for the second step, or could be narrowed around the first intensity information as well. For example, minus and plus 5 dB around the first intensity information could be chosen. The new boundaries can be slightly modified from being symmetrically arranged around the first frequency and intensity information (cf. FIG. 3) to avoid that the first information (frequency/intensity) would correspond to the middle position of the two-dimensional plane. With such variation, it could be avoided, that the patient could manipulate the results.

Figure 5:
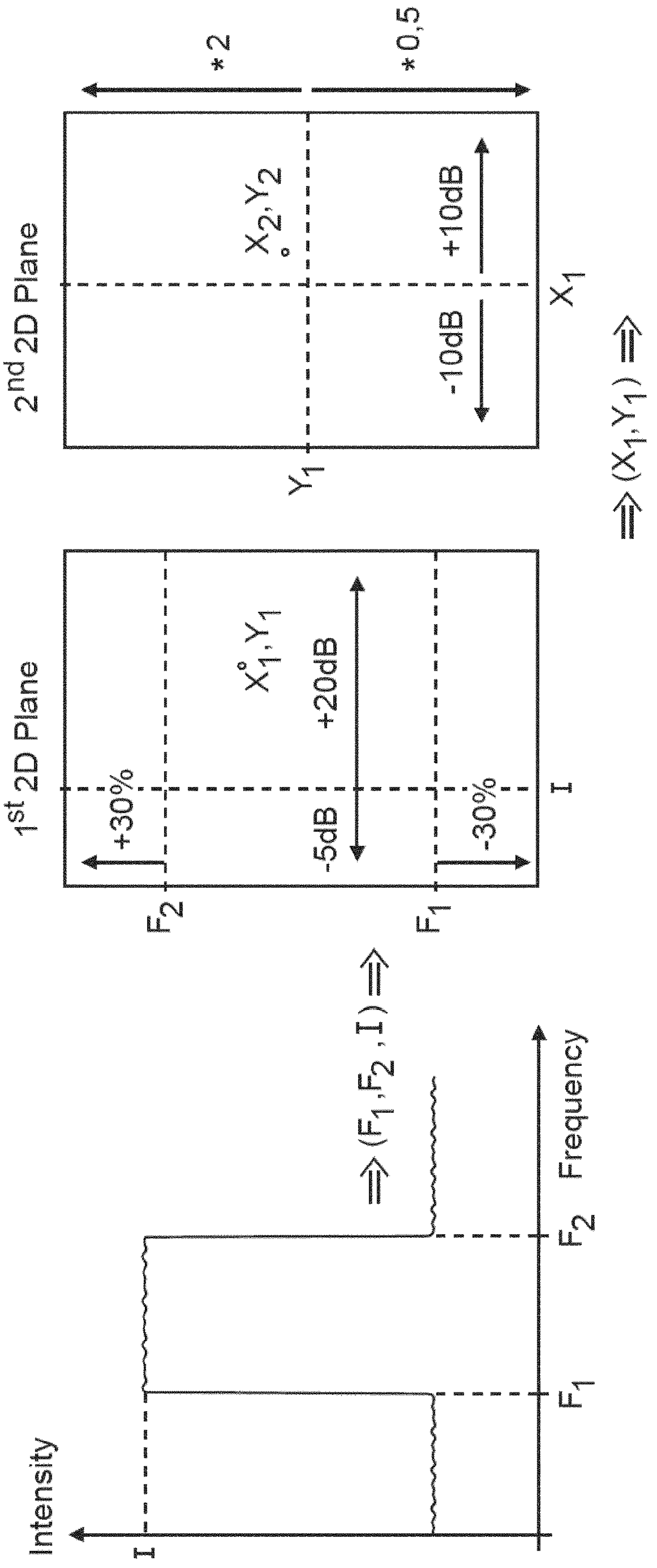
FIG. 5 illustrates a general sequence of the method of the invention according to one embodiment.

FIG. 5 is intended to illustrate a general sequence according to one embodiment of the invention. According to this sequence, the masking levels are determined, and the first intensity and frequency ranges are determined based on the masking levels. The first intensity and frequency range are depicted on a screen as two axes in a first 2-D plane, on which the patient can select the tone which comes closest to the patient's tinnitus tone. This tone is then used to define second intensity and frequency ranges, which are then depicted in a second 2-D plane, on which a further round of selection is made.

The patient is then asked in the third step to find its dominating tinnitus frequency on this modified two-dimensional plane. The outcome of the third step will be a second frequency/intensity information (i.e. final estimate of the patient's tinnitus tone). It is assumed, that the second frequency/intensity information is potentially more precise, since the frequency and intensity boundaries of the two-dimensional plane are usually narrower and thus allow a finer selection. Therefore, the second frequency/intensity information will be used as the final estimate.

In some embodiments, a quality of the result is determined. For instance, the deviation of the first and second information may be used to define the quality of the result. If both information (preliminary and final estimate) is very similar, the information is considered of high quality, if the information differs strongly, the quality is considered of low quality.

Quality can be measured on different scales, e.g. on a scale from 0% quality to 100% quality. Different implementations of the quality measure are possible and may be tested clinically. As one example, the quality could be defined by the sum of the factorized deviation in the frequency and intensity space, using the following equation:

$$Q=100\%-\text{Difference}(F1,F2)-0.5*\text{Difference}(I1,I2),$$

where the difference is defined as Difference(Z,W)=(Z−W)/((Z−FW)/2)) [%].

The quality may be further based on the patient's evaluation of the quality of the pitch matching. The evaluation may be conducted by asking the patient to answer one or more questions, for example, how good the patient considers the degree of match of the final estimate to the patient's tinnitus tone. As a non-limiting example, the factor reflecting the patient's evaluation may be defined by the following equation:

$$(-12.5*Z+50),$$

where Z=1, 2, 3 or 4 depending on the patient's answer (1: Quality was rated as very good, 4: Quality was rated as poor.)

The overall quality according to the above example could then be calculated as follows:

$$Q=100\%-\text{Difference}(F1,F2)-0.5*\text{Difference}(I1,I2)-(-12.5*Z+50),$$

where the parameters are defined as above.

In a further step, the resulting information (i.e. the final estimate of the patient's tinnitus tone) can be compared with several other test tones. Therefore, a pairwise comparison may be done. The tones that are compared to the final estimate resulting from step three could be: one octave up and one octave down (to test for octave confusion), 1.4 times the second frequency, 0.766 times the second frequency, 1.1 times the second frequency, 0.9 times the second frequency, 0.95 times the second frequency or 1.05 times the second frequency. Other test tones might be possible as well. The corresponding intensities are chosen such that the test tones and the tinnitus tone are perceived as of similar intensity (e.g. based on the audiogram-like test information). The patient may be allowed to listen to pairs of tones, one is a test tone and the other one is the result from the third step (i.e. the final estimate). After listening to both tones, the patient identifies the tone that fits his tinnitus best. Only if the frequency and intensity testing of the third step was properly done and resulted in a frequency/intensity that corresponds to the patient's tinnitus tone, the patient is assumed to be able to identify this tone as the tone that fits the tinnitus best in all the pair-wise comparisons.

The further step may serve as a validation step. For example, only if all pair-wise comparisons resulted in the frequency and intensity testing of step three, this step would be registered as passed. It is also possible to define the validation to be passed if only one pair-wise comparison testing failed (not resulting in frequency and intensity testing of step three).

After the validation step, the final result may be displayed and stored in the device. The final result may consist of the tinnitus information, namely frequency and intensity, the quality of the measurement (in %) and/or the result of the pair-wise comparison test (failed or passed).

Figure 6A:
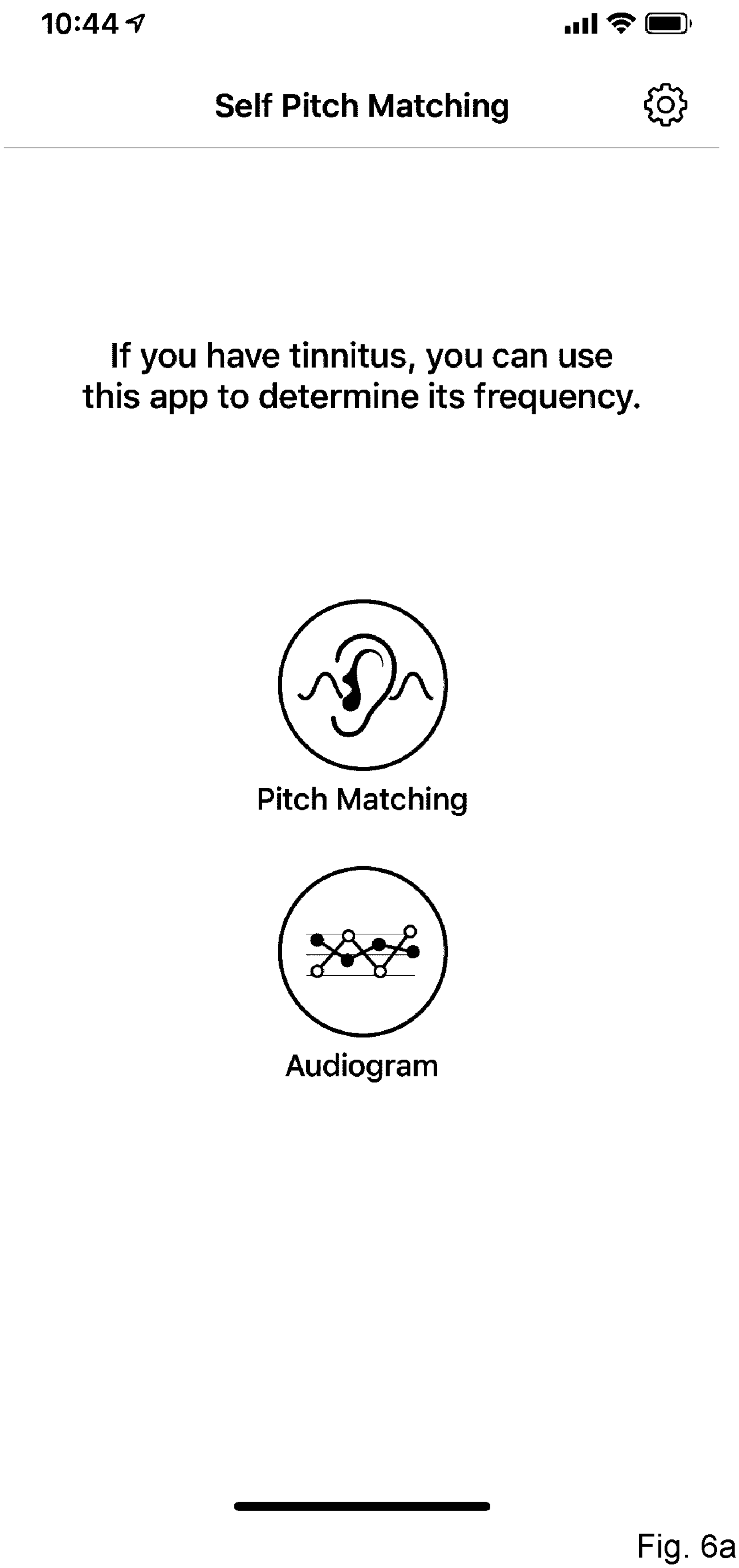
Figure 6B:
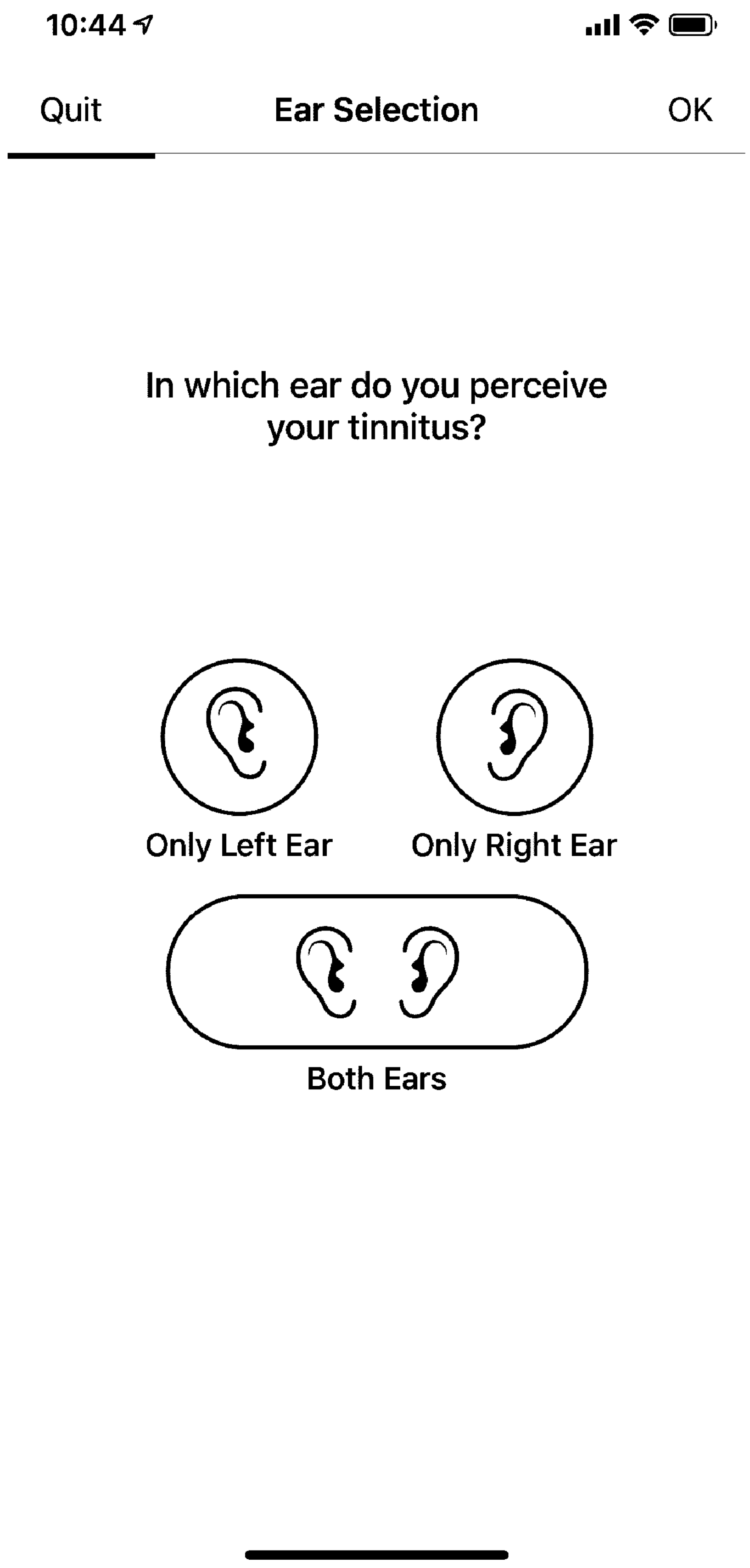
Figure 6C:
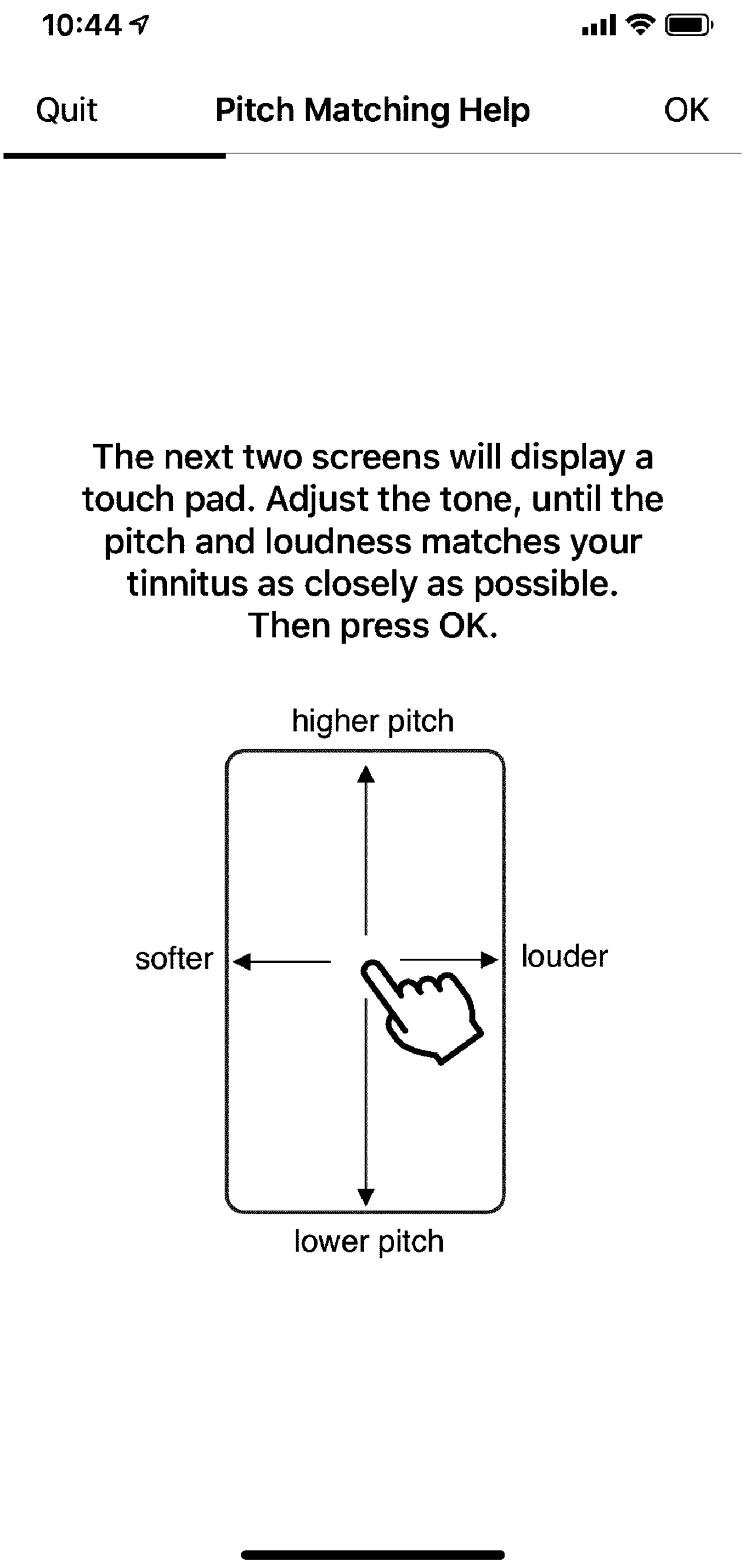
Figure 6D:
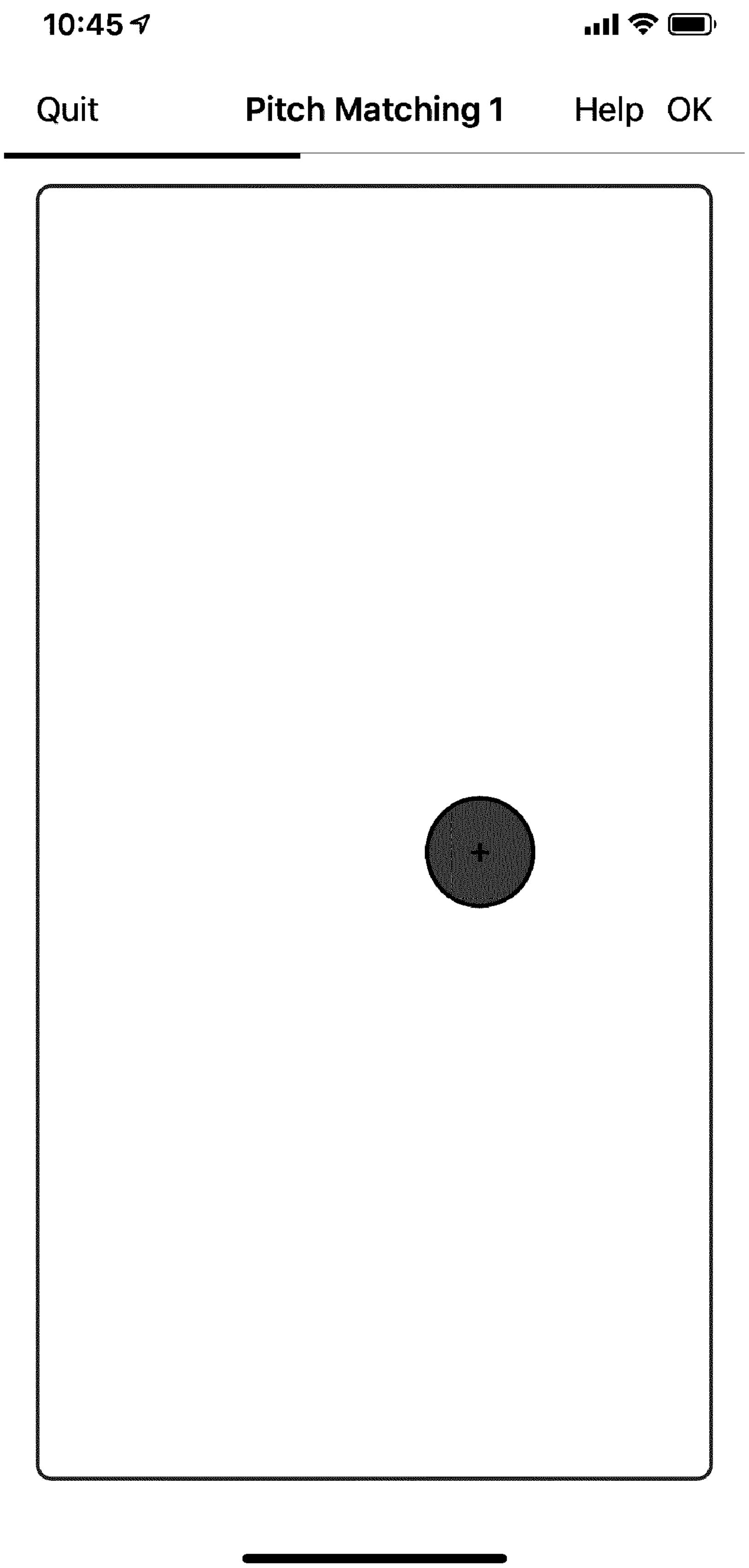
Figure 6E:
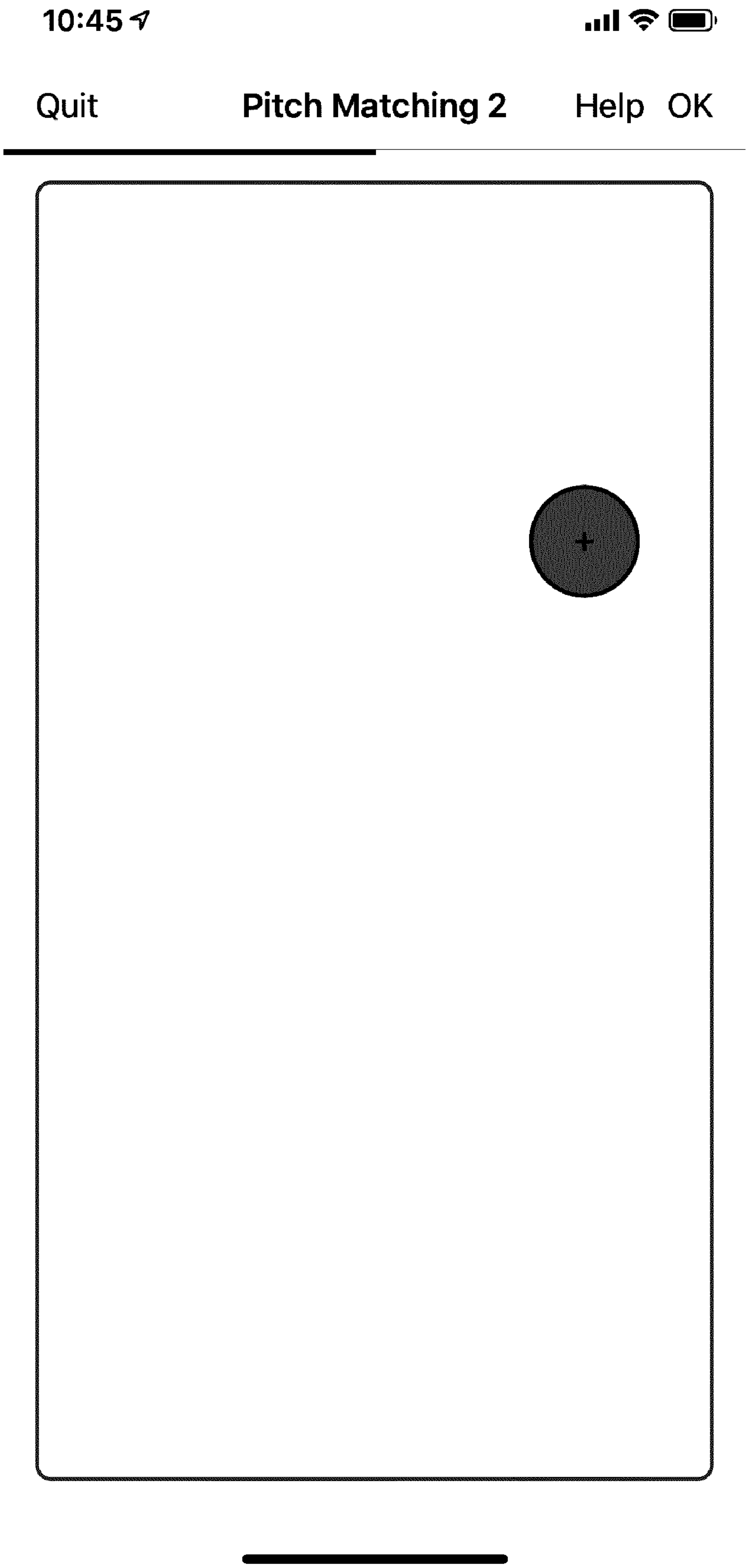
Figure 6F:
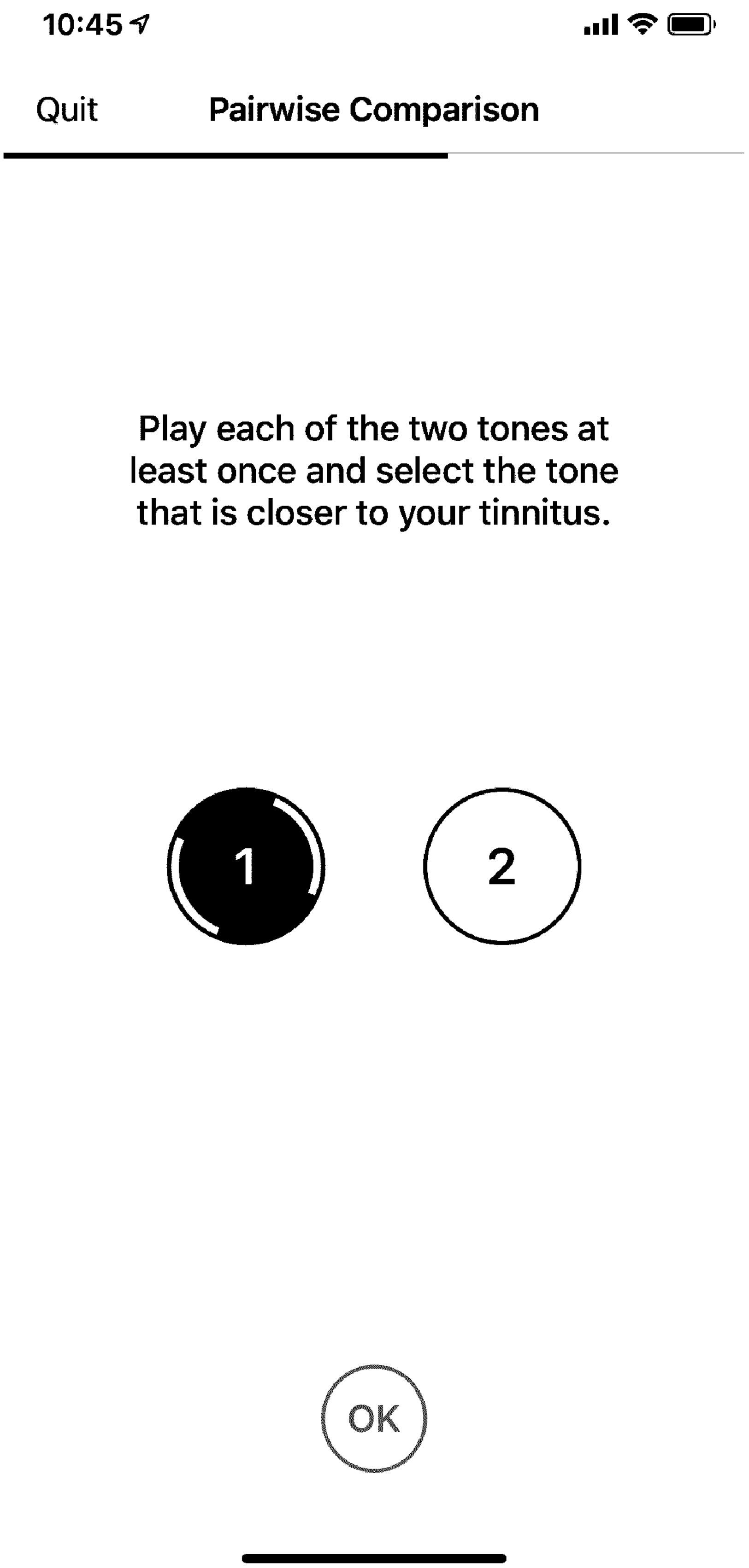
Figure 6G:
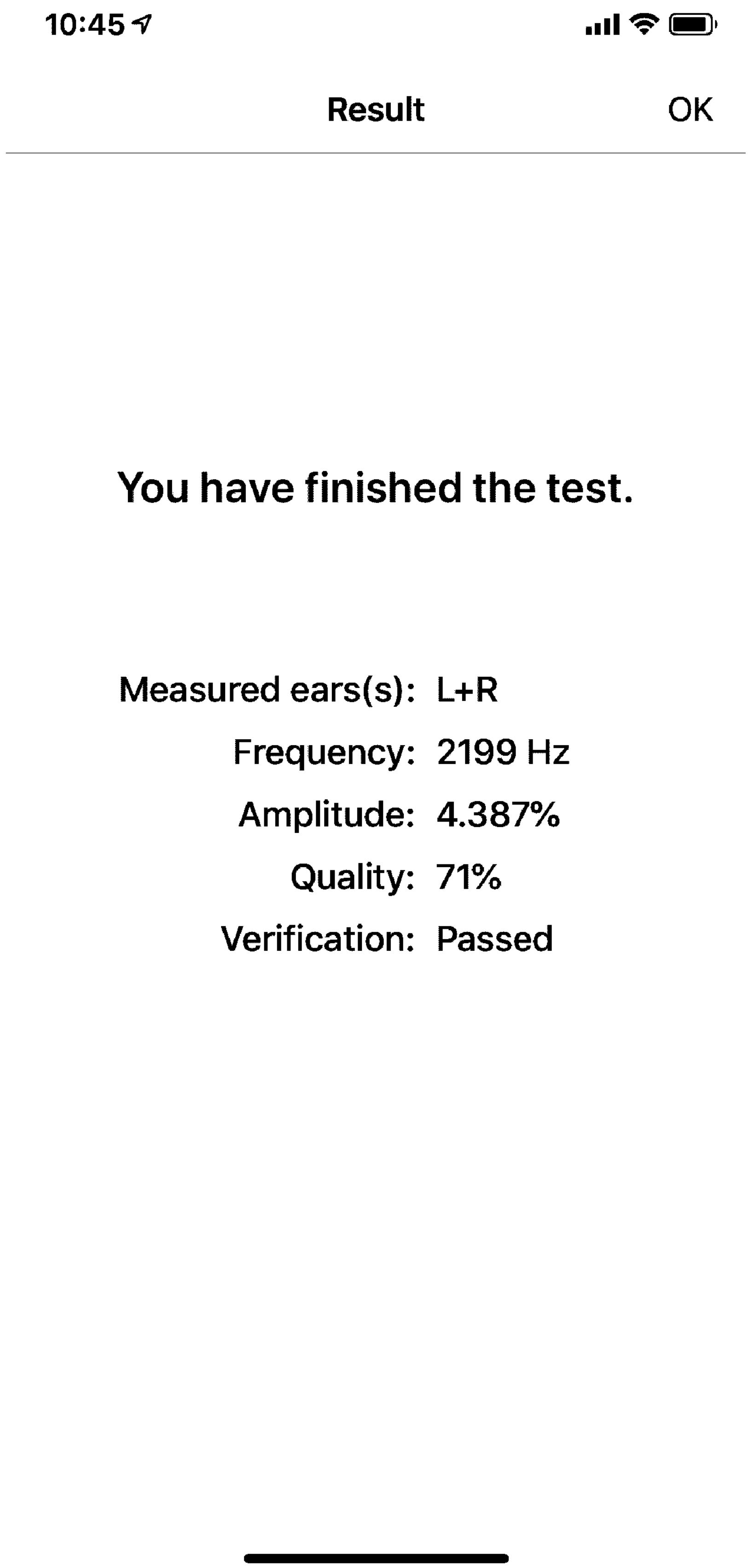

Referring to FIG. 6*a*-*h*, functionalities of the present invention according to various embodiments of the invention are illustrated. The functionalities may be part of a method as disclosed herein implemented as a computer program (app) executed by a digital processing device (smartphone). When the app is started, the patient may be guided through some functionalities along a predetermined path, whereas other functionalities may occur only when a patient selects them by pressing on a respective button on the screen. A first exemplary functionality may allow the patient to select between the pitch matching method as disclosed herein and an audiogram method, as illustrated in FIG. 6*a*. After selecting the pitch matching method, the patient may be asked to indicate, which ear(s) are to be analyzed (FIG. 6*b*). Before starting the pitch matching method as such, an instruction screen may pop up, briefly explaining the patient what to do (FIG. 6*c*). FIG. 6*d* shows an exemplary screen, on which the patient can vary the frequency and intensity of the first test tone in order to determine the preliminary estimate. FIG. 6*e* shows a corresponding exemplary screen for determining the final estimate. FIG. 6*f* shows an exemplary way that allows the patient to conduct the pair-wise testing. Afterwards, the results of the pitch matching method may be shown (FIG. 6*g*). FIG. 6*h* illustrates an exemplary screen that allows the patient to review previous pitch matching results.

The invention claimed is:

1. A method of determining a pitch of a patient's tinnitus tone, the method comprising:

presenting a first test tone to the patient;

varying, within a predetermined first frequency range or around a predetermined first intensity range, a frequency or an intensity of the first test tone to approximate the first test tone to the patient's tinnitus tone;

defining a second frequency range and a second intensity range around a preliminary estimate of the patient's tinnitus tone;

determining a final estimate of the patient's tinnitus tone by allowing the patient to listen to and vary frequency and intensity of a second test tone within the second frequency range and the second intensity range to approximate the second test tone to the patient's tinnitus tone; and determining a deviation of the preliminary estimate of the patient's tinnitus tone and the final estimate of the patient's tinnitus tone and determining reliability of the final estimate of the patient's tinnitus tone based on the deviation, wherein the reliability of the final estimate of the patient's tinnitus tone is defined to be higher the smaller the deviation, or vice versa, wherein the method is implemented on a digital processing unit of a device comprising an output unit for delivering test tones to the patient and a user interface for variation of the frequency and the intensity of the test tones by the patient.

2. The method of claim 1, wherein the user interface comprises a touch screen defining a two-dimensional plane, the touch screen configured so that sliding in a first dimension leads to an increase or decrease of the frequency and sliding in a second dimension leads to an increase or decrease of the intensity.

3. The method of claim 1, wherein the first frequency range is different than the second frequency range.

4. The method of claim 1, wherein the first frequency range and the first intensity range are determined based on a masking level of the patient, wherein the masking level is a lowest intensity of a given frequency band required to mask the patient's tinnitus tone.

5. The method of claim 4, wherein the masking level is determined by presenting at least one frequency band individually to the patient and increasing intensity of each of the at least one frequency band by a user until the patient detects that one of the at least one frequency band masks the patient's tinnitus tone.

6. The method of claim 1, wherein intensities within the first intensity range are scaled relative to same perceived intensities, wherein the same perceived intensities are intensities, which the patient perceives of substantially the same intensity at frequencies within the first frequency range.

7. The method of claim 6, wherein the same perceived intensities are determined based on the patient's threshold of perception of a plurality of test tones covering a plurality of frequencies adjacent or within the respective first or second frequency range.

8. The method of claim 1, further comprising:

performing at least one pair-wise testing, wherein in each of the at least one pair-wise testing the patient is allowed to listen to one pair of tones, the one pair of tones consisting of the final estimate of the patient's tinnitus tone and a test tone different thereof, and to choose the tone which closer matches the patient's tinnitus tone.

9. The method of claim 8, wherein the an intensity of one or more of the test tones is adapted to have the same perceived intensity with the final estimate of the patient's tinnitus tone.

10. The method of claim 8, wherein the method is registered as passed when the patient has chosen the final estimate of the patient's tinnitus tone as the tone which closer matches the patient's tinnitus tone in a majority of the at least one pair-wise testing.

11. A non-transitory storage medium storing instructions that are executable by a digital processing device to perform the method of claim 1.

12. The method of claim 1, wherein the first intensity range is different than the second intensity range.

13. The method of claim 1, wherein the first frequency range is different than the second frequency range, and wherein the first intensity range is different than the second intensity range.

14. The method of claim 1, wherein intensities within the second intensity range are scaled relative to same perceived intensities, wherein the same perceived intensities are intensities which the patient perceives of substantially the same intensity at frequencies within the second frequency range.

15. A digital processing device comprising:

an output unit for delivering test tones to a patient;

an user interface for varying frequency and intensity of the test tones by a user; and a control unit in functional communication with the output unit and the user interface, the control unit comprising a digital processing unit for performing the method of claim 1.

16. The digital processing device of claim 15, wherein the user interface comprises a touch screen defining a two-dimensional plane, which is configured so that sliding in a first dimension leads to an increase or decrease of the frequency and sliding in a second dimension leads to an increase or decrease of the intensity.

* * * * *